(12) United States Patent
Oshima et al.

(10) Patent No.: US 8,705,026 B2
(45) Date of Patent: Apr. 22, 2014

(54) INSPECTION APPARATUS

(75) Inventors: Yoshimasa Oshima, Yokohama (JP);
Yuta Urano, Yokohama (JP); Toshiyuki Nakao, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 38 days.

(21) Appl. No.: 13/597,553

(22) Filed: Aug. 29, 2012

(65) Prior Publication Data

US 2012/0320373 A1 Dec. 20, 2012

Related U.S. Application Data

(63) Continuation of application No. 13/368,764, filed on Feb. 8, 2012, now Pat. No. 8,264,679, which is a continuation of application No. 12/506,421, filed on Jul. 21, 2009, now Pat. No. 8,120,766.

(30) Foreign Application Priority Data

Sep. 10, 2008 (JP) .................................. 2008-231640

(51) Int. Cl.
*G01N 21/00* (2006.01)
(52) U.S. Cl.
USPC ...................................... 356/237.2; 356/237.5
(58) Field of Classification Search
USPC ............................................ 356/237.2, 237.5
See application file for complete search history.

(56) References Cited

U.S. PATENT DOCUMENTS

| | | | |
|---|---|---|---|
| 5,712,701 A * | 1/1998 | Clementi et al. | 356/237.2 |
| 6,034,776 A | 3/2000 | Germer et al. | |
| 6,639,662 B2 | 10/2003 | Vaez-Iravani et al. | |
| 7,002,677 B2 | 2/2006 | Bevis et al. | |
| 7,557,911 B2 * | 7/2009 | Oka et al. | 356/237.2 |
| 7,764,367 B2 * | 7/2010 | Matsui | 356/237.2 |
| 7,773,210 B2 * | 8/2010 | Oka et al. | 356/237.1 |
| 2008/0024765 A1 * | 1/2008 | Oka et al. | 356/73 |
| 2008/0174764 A1 * | 7/2008 | Matsui | 356/73 |
| 2008/0304057 A1 * | 12/2008 | Bills et al. | 356/237.5 |
| 2009/0244529 A1 * | 10/2009 | Oka et al. | 356/237.2 |
| 2010/0259750 A1 * | 10/2010 | Oka et al. | 356/237.3 |

FOREIGN PATENT DOCUMENTS

| | | |
|---|---|---|
| JP | 09-304289 | 11/1997 |
| JP | 2001-255278 | 9/2001 |
| JP | 2002-340537 | 11/2002 |

* cited by examiner

*Primary Examiner* — Roy M Punnoose
(74) *Attorney, Agent, or Firm* — Antonelli, Terry, Stout & Kraus, LLP.

(57) ABSTRACT

An inspection method and apparatus for detecting defects or haze of a sample, includes illuminating light to the sample from an oblique direction relative to a surface of the sample with an illuminator, detecting first scattered light at a forward position relative to an illuminating direction from the sample with a first detector, detecting sec and scattered light at a sideward or backward position relative to the illuminating direction from the sample with a second detection, and processing a first signal of the first scattered light and a second signal of the second scattered light with different weighting for the first signal and for the second signal with a processor.

26 Claims, 8 Drawing Sheets

INSPECTION APPARATUS

CROSS REFERENCE TO RELATED APPLICATION

This application is a continuation of U.S. application Ser. No. 13/368,764, filed Feb. 8, 2012, now U.S. Pat. No. 8,264,679 which is a continuation of U.S. application Ser. No. 12/506,421, filed Jul. 21, 2009, now U.S. Pat. No. 8,120,766, the contents of which are incorporated herein by reference.

BACKGROUND OF THE INVENTION

The present invention relates to an apparatus for inspecting microscopic contamination, defects, and haze existing on the surfaces of samples such as semiconductor substrates.

In manufacturing lines for semiconductor substrates, thin-film substrates, and the like, the defects and contamination existing on the surfaces of semiconductor substrates, thin-film substrates, or the like, are inspected to maintain or improve respective product yield rates. For example, before circuit patterns are formed on samples such as semiconductor substrates, these samples require the detection of microscopic surface defects and contamination of 0.05 microns or less in diameter. In order to detect these microscopic surface defects and contamination, such a conventional inspection apparatus as described in Patent Document 1 (JP-H09-304289-A) irradiates the surface of a sample with a laser beam condensed to several tens of microns, and acquires/detects the light scattered from defects or contamination. In addition, in conventional techniques for discriminating the kinds of defects, the directionality of the light scattered from a defect is discriminated by detecting the scattered light from multiple directions, as in Patent Document 1 (JP-2001-255278-A).

For even more accurate detection of defects and/or contamination, it is important to reduce the amount of light scattered by the roughness (haze) existing on the substrate surface. Techniques for implementing the reduction are described in Patent Document 3 (U.S. Pat. No. 6,034,776), Patent Document 4 (U.S. Pat. No. 6,639,662), and Patent Document 5 (U.S. Pat. No. 7,002,677).

SUMMARY OF THE INVENTION

The distribution of the light scattered by defects as small as about 1/10th of the illumination wavelength becomes isotropic. For this reason, additive averaging of the signals that have been detected from multiple directions improves a signal-to-noise (S-N) ratio, thus allowing micro-defect detection. Noise is shot noise due to the detection of the scattered light originating from surface roughness, and the shot noise is random noise. If the shot noise contained in the signals that have been detected from multiple directions is substantially of the same level between the signals, additive averaging will reduce the noise level in proportion to the square root of the number of detecting directions. The intensity distribution of the scattered light originating from surface roughness, however, generally has an offset and thus since the shot noise contained in the multi-directionally detected signals is not uniform, additive averaging of these signals decreases in effectiveness.

The present invention provides an inspection apparatus intended to solve the above problems, capable of detecting microscopically smaller defects, and constructed to achieve even more accurate detection of roughness.

The present invention focuses attention on the fact that the scattered light originating from the surface roughness of silicon or other metallic films will be distributed more strongly at positions closer to the starting position of the scattering. In perspective of this fact, the invention provides an inspection apparatus that detects micro-defects by using, of all signals that multi-azimuth and multi-elevation angle detection optics has detected, only signals primarily of a forward-scattered beam of light, only a signal of the forward-scattered beam of light, only signals primarily of sideward- and backward-scattered beams of light, or only a signal of the backward-scattered beam of light.

Typical aspects of the invention that are disclosed in this application are outlined below.

(1) An inspection apparatus for detecting defects and haze on a surface of a sample comprises: illumination optics for emitting light to illuminate an inspection region on the surface of the sample from an oblique direction relative to the inspection region; first detection optics provided at one or a plurality of forward positions relative to the direction of the illumination by the illumination optics, the detection optics being adapted to detect the light scattered from the inspection region, in a forward direction relative to the direction of the illumination by the illumination optics; second detection optics provided at one or a plurality of sideward or backward positions relative to the direction of the illumination by the illumination optics, the detection optics being adapted to detect the light scattered from the inspection region, in sideward or backward directions relative to the direction of the illumination by the illumination optics; and a signal-processing unit for detecting defects on the surface of the sample on the basis of a signal detected by the first detection optics, the unit further detecting haze on the surface of the sample on the basis of a signal detected by the second detection optics.

(2) The inspection apparatus according to above item (1), wherein the first detection optics has plural sets of forward detection optics; and the signal-processing unit detects the defects on the surface of the sample by performing either additions, subtractions, divisions, or averaging, between a plurality of signals obtained by the respective plural sets of forward detection optics, or by using a signal derived from processing based upon a combination of the arithmetic operations.

(3) The inspection apparatus according to above item (1), wherein the second detection optics has plural sets of sideward detection optics or plural sets of backward detection optics; and the signal-processing unit detects the haze on the surface of the sample by performing either additions, subtractions, divisions, or averaging, between a plurality of signals obtained by the plural sets of sideward detection optics or the plural sets of backward detection optics, or by using a signal derived from processing based upon a combination of the arithmetic operations.

(4) The inspection apparatus according to above item (1), wherein the illumination optics conducts illumination with p-polarized illumination light and the first detection optics detects only p-polarized components of the scattered light.

(5) An inspection apparatus for detecting defects and haze on a surface of a sample comprises: illumination optics for emitting light to illuminate an inspection region on the surface of the sample from an oblique direction relative to the inspection region; plural sets of detection optics arranged with at least a plurality of azimuth angles different from each other, the plural sets of detection optics being adapted to detect in the lump the respective beams of light scattered from the inspection region, at the respective arrangement angles; and a signal-processing unit for detecting defects on the surface of the sample on the basis of a signal obtained by performing a first weighting process between a plurality of signals detected by the respective plural sets of detection optics, the unit further detecting haze on the surface of the sample on the basis of a signal obtained by performing a second weighting process between the plurality of signals.

(6) The inspection apparatus according to above item (5), wherein: after performing a process such that a rate of a signal obtained by the detection optics provided at one or plural forward positions relative to the direction of the illumination by the illumination optics, to a signal obtained by the detection optics provided at one or plural sideward or backward positions relative to the illuminating direction, will be great, the signal-processing unit detects the defects on the surface of the sample on the basis of a signal obtained by adding the detected signals.

(7) The inspection apparatus according to above item (5), wherein: after performing a process such that a rate of a signal obtained by the detection optics provided at one or plural sideward or backward positions relative to the direction of the illumination by the illumination optics, to a signal obtained by the detection optics provided at one or plural forward positions relative to the illuminating direction, will be great, the signal-processing unit detects the haze on the surface of the sample on the basis of a signal obtained by adding the detected signals.

These and other objects, features and advantages of the invention will be apparent from the following more particular description of preferred embodiments of the invention, as illustrated in the accompanying drawings.

DESCRIPTION OF THE EMBODIMENTS

An embodiment of an inspection apparatus according to the present invention will be described hereunder.

Figure 1:
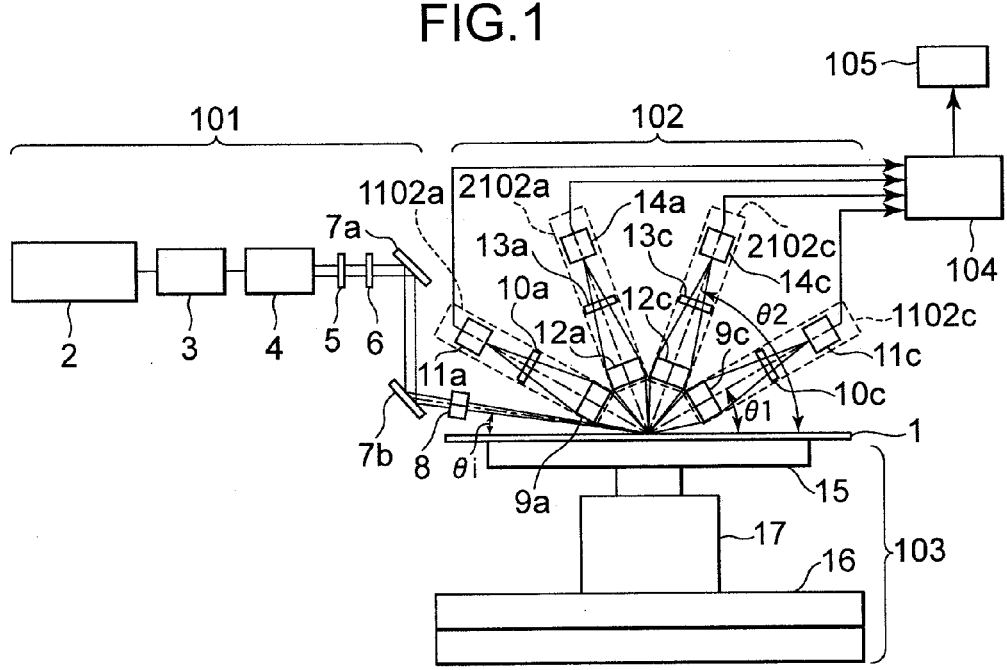
FIG. 1 is a side view of an inspection apparatus according to the present invention.
Figure 2:
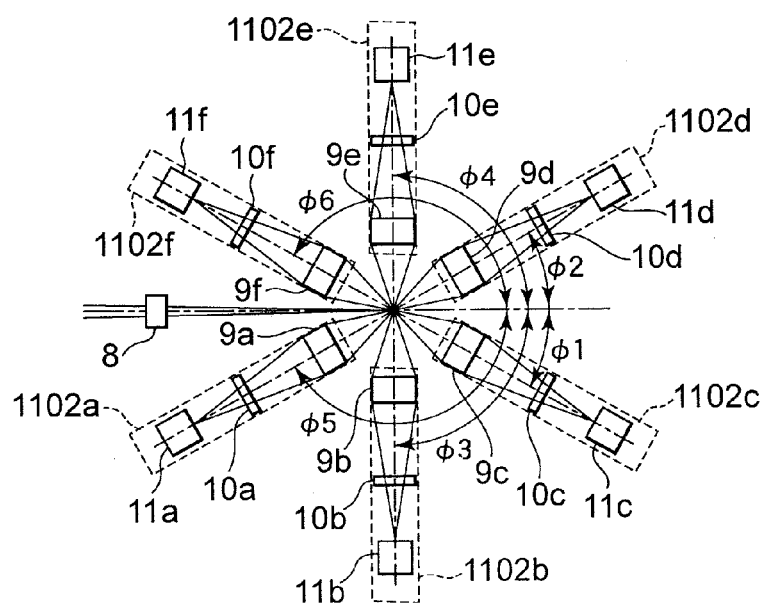
FIG. 2 is a plan view of low-angle detection optics in the inspection apparatus according to the present invention.
Figure 3:
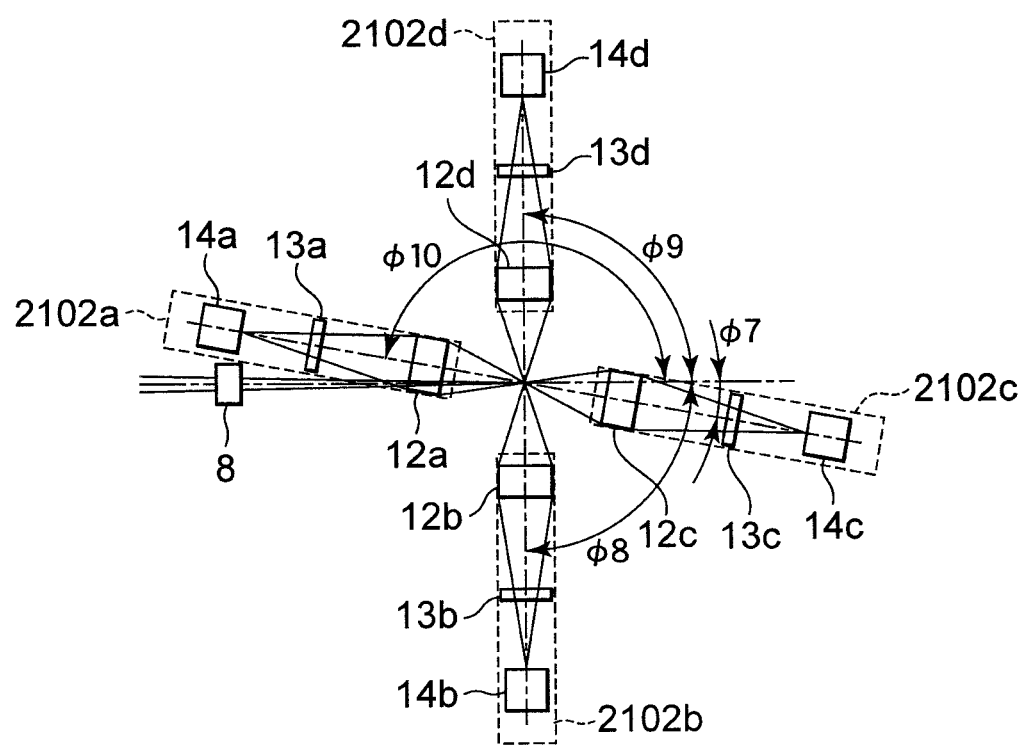
FIG. 3 is a plan view of high-angle detection optics in the inspection apparatus according to the present invention.

FIGS. 1, 2, 3 show an example of an inspection apparatus for detecting defects/contamination on a semiconductor wafer that may exist before circuit patterns are formed thereon. FIG. 1 is a side view of the inspection apparatus, FIG. 2 is a plan view of low-angle detection optics, and FIG. 3 is a plan view of high-angle detection optics. As shown in FIG. 1, the inspection apparatus according to the present invention includes illumination optics 101, detection optics 102 including a plurality of sets of detection optics (such as 1102a), a wafer stage 103, a signal-processing unit 104, and a display unit 105.

The illumination optics 101 includes a laser light source 2, an attenuator 3, a beam expander 4, wave retarders 5, 6, mirrors 7a, 7b, and a condensing lens 8, as appropriate. An exit laser beam emitted from the laser light source 2 is controlled to a necessary amount of light by the attenuator 3. Next after being expanded in diameter by the beam expander 4, the laser beam is polarized in preset directions by the wave retarders 5, 6, and then changed in illumination optical path by the mirrors 7a, 7b, as appropriate. The beam is then condensed by the condensing lens 8 to illuminate a detection area on a wafer 1. The wave retarders 5, 6 change the polarization state of the illumination light to s-polarization, p-polarization, or circular polarization, at appropriate timing. An illumination elevation angle $\theta i$ of the oblique illumination optics 101 here is desirably from 5 to 25 degrees. A cylindrical lens or the like may be used to obtain linear illumination light on the wafer 1.

The attenuator 3 is constructed using, for example, a half-wave retarder and a polarized beam splitter (hereinafter, called the PBS). The exit beam (linearly polarized light) from the laser light source 2 is inclined at a polarizing angle by the half-wave retarder, thus changing in the amount of light when passed through the PBS. Rotation of the half-wave retarder changes the polarized-light axis, making the amount of light controllable.

The detection optics 102 is formed by a combination of multiple sets of low-angle detection optics and high-angle detection optics, each set of detection optics including scattered-light detection lenses 9 (9a-9f), 12 (12a-12d), beam analyzers 10 (10a-10f), 13 (13a-13d), and photoelectric transfer elements 11 (11a-11f), 14 (14a-14d), as appropriate, so that the light scattered from a defect or contamination present in the detection area of the wafer 1 will be condensed substantially on beam-receiving surfaces of the photoelectric transfer elements 11, 14 by the detection lenses 9, 12. The photoelectric transfer elements 11, 14 will each generate an electrical signal of a magnitude proportional to the amount of scattered light received, and then process the signal via a signal-processing circuit (not shown) to detect the defect or contamination and hence a size and position thereof. The photoelectric transfer elements 11, 14 used to receive the scattered light that has been condensed by the corresponding sets of detection optics, and transform the light into electrical signal form, are, for example, TV cameras, CCD linear sensors, TDI sensors, or photomultipliers. The analyzers 10, 13 are used to detect only components polarized in specific directions, the polarized components being contained in the scattered light. A detection elevation angle (central angle) $\theta_1$ of the low-angle detection optics desirably ranges from about 15 degrees to about 35 degrees, and a desirable detection elevation angle (central angle) $\theta_2$ of the high-angle detection optics ranges from about 45 degrees to about 70 degrees.

The wafer stage 103 includes a chuck 15 for holding the wafer 1, a rotating mechanism 17 for rotating the wafer 1, and a rectilinear feed mechanism 16 for moving the wafer 1 rectilinearly in a radial direction. Contamination/defect detection in all regions of the wafer 1 becomes possible by performing horizontal rotational scanning and rectilinear moving of the wafer with the wafer stage 103.

FIG. 2 is a plan view of the low-angle detection optics which forms part of the detection optics 102. Defects can be detected from multiple directions by arranging a plurality of sets of low-angle detection optics at azimuth angles different from each other. In this case, a desired signal can have its S-N ratio improved if one optimal signal of all signals obtained by the photoelectric transfer elements of each set of detection optics is selected according to particular directionality of the scattered-light intensity distribution or if additions, subtractions, divisions, averaging, or other arithmetic operations are performed between a plurality of signals selected from the obtained signals. That is to say, since the scattered light originating from the haze on the surface of the wafer 1 will be distributed more strongly at positions closer to a starting position of the scattering, microscopically smaller defects can be detected at an improved S-N ratio by using only a signal that forward detection optics 1102c or 1102d for detecting the light scattered forward with respect to the illuminating direction of the oblique illumination light has acquired, or by performing an addition and/or other processes between both signals acquired by the forward detection optics 1102c and 1102d. Conversely, the haze can be detected using signals that have been acquired by sideward detection optics 1102b and 1102e or backward detection optics 1102a and 110f for detecting the light scattered sideward or backward. In an alternative method of defect detection, the signals that each set of detection optics has acquired may be weighted according to the kind of object to be detected, and then the values may be provided with processing such as addition. The weighting may be associated with noise intensity of each detected signal by relative comparison, for example, or can be performed by actively providing a difference in sensitivity between the photoelectric transfer elements in advance. Defect detection at an improved S-N ratio, for instance, can be implemented by integrating data so that a rate of the signals obtained by detecting forward scattered light, to the signals obtained by detecting sideward or backward scattered light, will be great, and then using a value obtained from adding these signals. Haze detection can be achieved by integrating data so that a rate of the signals obtained by detecting sideward or backward scattered light, to the signals obtained by detecting forward scattered light, will be great, and then using a value obtained from adding these signals.

For the low-angle six-direction detection shown in the present embodiment, approximate detection azimuth angles (central angles) with respect to the illuminating direction desirably range from 20° to 50° ($\phi_1$), −20° to −50° ($\phi_2$), 70° to 110° ($\phi_3$), −70° to −110° ($\phi_4$), 130° to 160° ($\phi_5$), and −130° to −160° ($\phi_6$). The detection form, however, is not limited to six-direction detection, and provided that the plurality of sets of detection optics are arranged at a plurality of azimuth angles to allow detection from, for example, four directions or eight directions, the number of sets of detection optics arranged and/or the azimuth angles may be changed as appropriate.

FIG. 3 is a plan view of the high-angle detection optics which forms part of the detection optics 102. Defects can be detected from multiple directions by arranging a plurality of sets of high-angle detection optics at azimuth angles different from each other. In this case, as in the low-angle detection optics, the improvement of a desired signal in S-N ratio and/or the detection of haze can be achieved if one optimal signal of all signals obtained by the photoelectric transfer elements of each set of detection optics is selected according to the particular directionality of the scattered-light intensity distribution or if additions, subtractions, divisions, averaging, or other arithmetic operations are performed between a plurality of signals selected from the obtained signals. For the high-angle four-direction detection shown in the present embodiment, approximate desirable detection azimuth angles (central angles) with respect to the illuminating direction are desirably ±10° ($\phi_7$), 80° to 110° ($\phi_8$), −80° to −110° ($\phi_9$), and 180°±10° ($\phi_{10}$). The detection form, however, is not limited to four-direction detection and the number of sets of detection optics arranged and/or the azimuth angles can be changed as appropriate.

An example in which only the optimal signal of all signals acquired in the multiple sets of low-angle detection optics is used according to the particular directionality of the scattered-light intensity distribution or only better signals of all signals acquired in the multiple sets of high-angle detection optics are selected as appropriate and undergo arithmetic addition, for example, has been shown and described in the present embodiment. The defect or haze detection form of the detection optics, however, is not limited to the above. The two kinds of detection optics may be adapted, for example, to detect defects or haze by selecting, as appropriate, only the optimal signal of all signals acquired collectively in both the low-angle detection optics and the high-angle detection optics, or by selecting as appropriate and performing additions upon only better signals of all acquired signals. In addition, combining the low-angle detection optics and the high-angle detection optics makes a dynamic range extendible by switching control to the photoelectric transfer element 14a if, for example, the photoelectric transfer element 11a saturates. Furthermore, as described later herein, the kind of defect can be discriminated by comparing the signals of the low-angle detection optics and those of the high-angle detection optics. However, there is no absolute need for both the multiple sets of low-angle detection optics and the multiple sets of high-angle detection optics to be provided, and microscopic defects and haze are detectible by providing multiple sets of detection optics oriented in at least two of the four directions (forward, sideward, and backward) relative to the illuminating direction of oblique illumination. While the elevation angle shown and described by way of example in the above embodiment has been the same between the multiple sets of low-angle detection optics or between the multiple sets of high-angle detection optics, the elevation angle is not limited to this example and can differ between the multiple sets of low-angle or between the multiple sets of high-angle detection optics.

Figure 4:
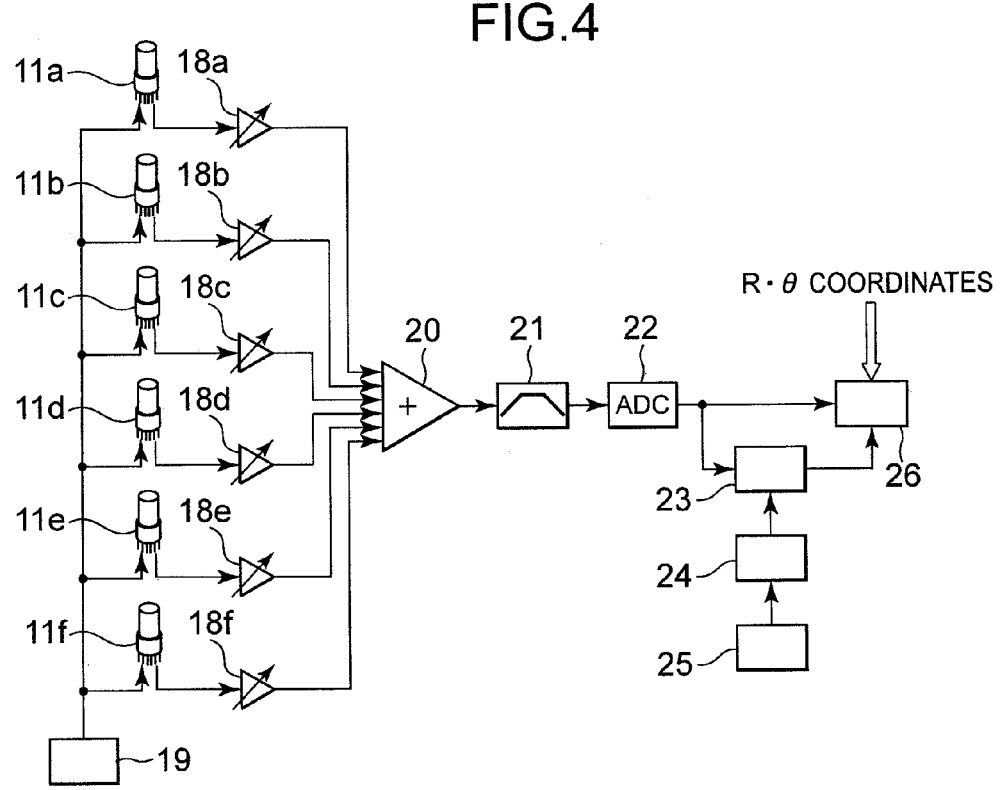
FIG. 4 is a diagram showing an example of a signal-processing circuit.

FIG. 4 shows an example of a signal-processing scheme of the low-angle detection optics, employing photomultipliers as the photoelectric transfer elements 11. The photomultipliers 11 require high-voltage application and are powered from a high-voltage DC power supply 19. Output signals from each photomultiplier 11 undergo current-voltage conversion and necessary voltage amplification before being added in an adder 20. In this sequence, the amplifiers 18 (18a-18f) regulate amplification factors of each photomultiplier to correct any differences in sensitivity between the photomultipliers 11.

Figure 5:
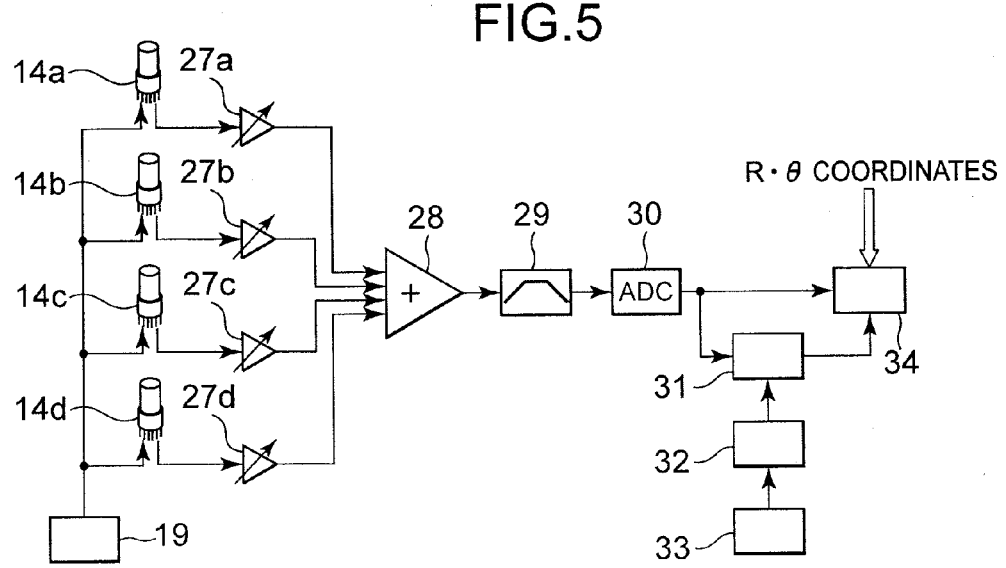
FIG. 5 is a diagram showing another example of a signal-processing circuit.

After removal of DC components and unnecessary noise components from an output signal of the adder 20 by a bandpass filter 21, this output signal is converted into a digital signal by an A/D converter 22. The A/D converter 22 has its output compared with a threshold level by a comparator 23. If the threshold level is exceeded, the above digital signal level is stored with R·θ coordinates into a defect memory 26. The threshold level is assigned from a CPU (not shown) to a latch 24 via an interface 25. Content of the defect memory 26 is read out from the CPU and then used for defect map display, defect classification, and other purposes. FIG. 5 shows an example of a signal-processing scheme of the high-angle detection optics, details of this scheme being the same as the signal-processing scheme of the low-angle detection optics as shown in FIG. 4.

During p-polarized illumination, the intensity distribution of the scattered light originating from a micro-defect (measuring about 1/5 or less of the illumination wavelength) becomes isotropic and each detected signal (S) takes substantially the same value. The shot noise (N) output from each photomultiplier 11 is random, with the output signal of the photomultiplier 11 becoming S/N in signal-to-noise (S-N) ratio. Upon additive averaging of all detected signals as shown in FIGS. 4 and 5, if the shot noise (N) output from each photomultiplier 11 is substantially of the same level, the shot noise will be averaged (a square root of the second sum will be extracted) to become $1/\sqrt{6}$ (for six-direction detection), which will improve the S-N ratios of each detected signal by a factor of $\sqrt{6}$, thus making micro-defect detection possible by independent signal processing for each photomultiplier 11.

However, the scattered light originating from the surface roughness of silicon (Si) and metallic films such as tungsten (W) or copper (Cu), does not become isotropic and is distributed more strongly at positions closer to a starting position of the scattering. If the scattered light due to the roughness detected by the photomultiplier 11 has an intensity "Su", the shot noise occurring in the photomultiplier 11 will be proportional to $\sqrt{Su}$ and forward detection (11c, 11d), sideward detection (11b, 11e), and backward detection (11a, 11f) will make $\sqrt{Su}$ greater in that order. Even such additive averaging of the multi-directional detection signals as shown in FIGS. 4, 5, therefore, will not improve the respective S-N ratios and will only cause each to be governed by the S-N ratio of a backward detection signal of a higher noise level.

An example of a signal-processing scheme in which the influence of the shot noise is reduced for improved S-N ratios is described below with reference to FIG. 6. The following description assumes that p-polarization by which a strong electric field is obtainable near the wafer surface is used for illumination, that only forward scattered light, because of its small amount of roughness-originated scattering, is applied to defect detection, and that since sideward scattered light and backward scattered light are large in the amount of roughness-originated scattering, both sideward scattered light and backward scattered light are applied to haze (roughness information) detection.

Figure 6:
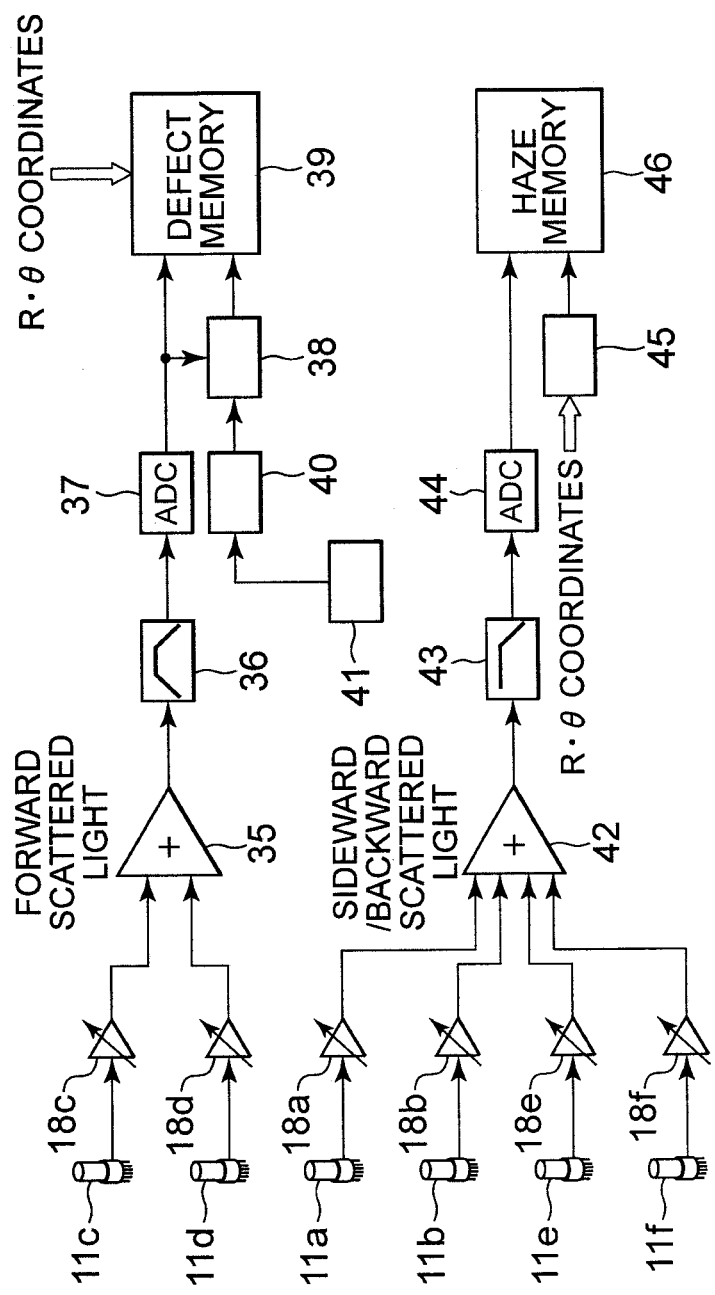
FIG. 6 is a diagram showing an example of a signal-processing circuit for achieving defect detection and haze detection.

As shown in FIG. 6, signal processing that differs between forward scattered light and sideward/backward scattered light takes place in the signal-processing scheme of the signal-processing unit 104. For the detection of forward scattered light, an adder 35 conducts additive averaging between the output signals of the amplifiers 18c and 18d connected to output terminals of the photomultipliers 11c and 11d, respectively, provided in the detection optics sets 1102c and 1102d for detecting the forward scattered light. After removal of DC components and unnecessary noise components from an output signal of the adder 35 by a band-pass filter 36, this output signal is converted into a digital signal by an A/D converter 37. The A/D converter 37 has its output compared with a threshold level by a comparator 38. If the threshold level is exceeded, the above digital signal level is stored with R·θ coordinates into a defect memory 39. The threshold level is assigned from a CPU (not shown) to a latch 40 via an interface 41. Content of the defect memory 39 is read out from the CPU and then used for defect map display, defect classification, and other purposes.

For the detection of sideward/backward scattered light, an adder 42 conducts additive averaging between the output signals of the amplifiers 18a, 18b, 18e, and 18f connected to output terminals of the photomultipliers 11a, 11b, 11e, and 11f, respectively, provided in the detection optics sets 1102a, 1102b, 1102e, and 1102f for detecting the sideward/backward scattered light. After removal of high-frequency components from an output signal of the adder 42 by a low-pass filter 43, this output signal is converted into a digital signal by an ND converter 44. The A/D converter 44 stores the digital signal level into a haze memory 46. The storage is performed in synchronization with a timing signal created on the basis of R·θ coordinates by a timing circuit 45. Content of the haze memory 46 is read out from the CPU (not shown) and then used for haze map display and other purposes. An example of adding all photomultiplier output signals has been shown, but as described above, the present invention is not limited to this example and only a part of the signals that has been selected may be added or can undergo other appropriate arithmetic operations such as subtraction, division, and/or averaging.

Scattered light due to roughness contains polarization information. Accordingly, insertion of the beam analyzers 10c and 10d into the defect detection optics sets for detecting the defects that cause the forward scattered light reduces the amount of incidence of the scattered light due to roughness, hence improving the S-N ratio. When the illumination light is p-polarized light, an insertion angle of the analyzers 10c, 10d is desirably that which lets the p-polarized light pass through. Conversely for haze detection, since insertion of analyzers into the defect detection optics for detecting the haze that causes sideward/backward scattered light reduces the amount of haze information as well, the analyzers 10a, 10b, 10e, 10f are desirably not inserted into optical paths of these detection optics sets.

Figure 7:
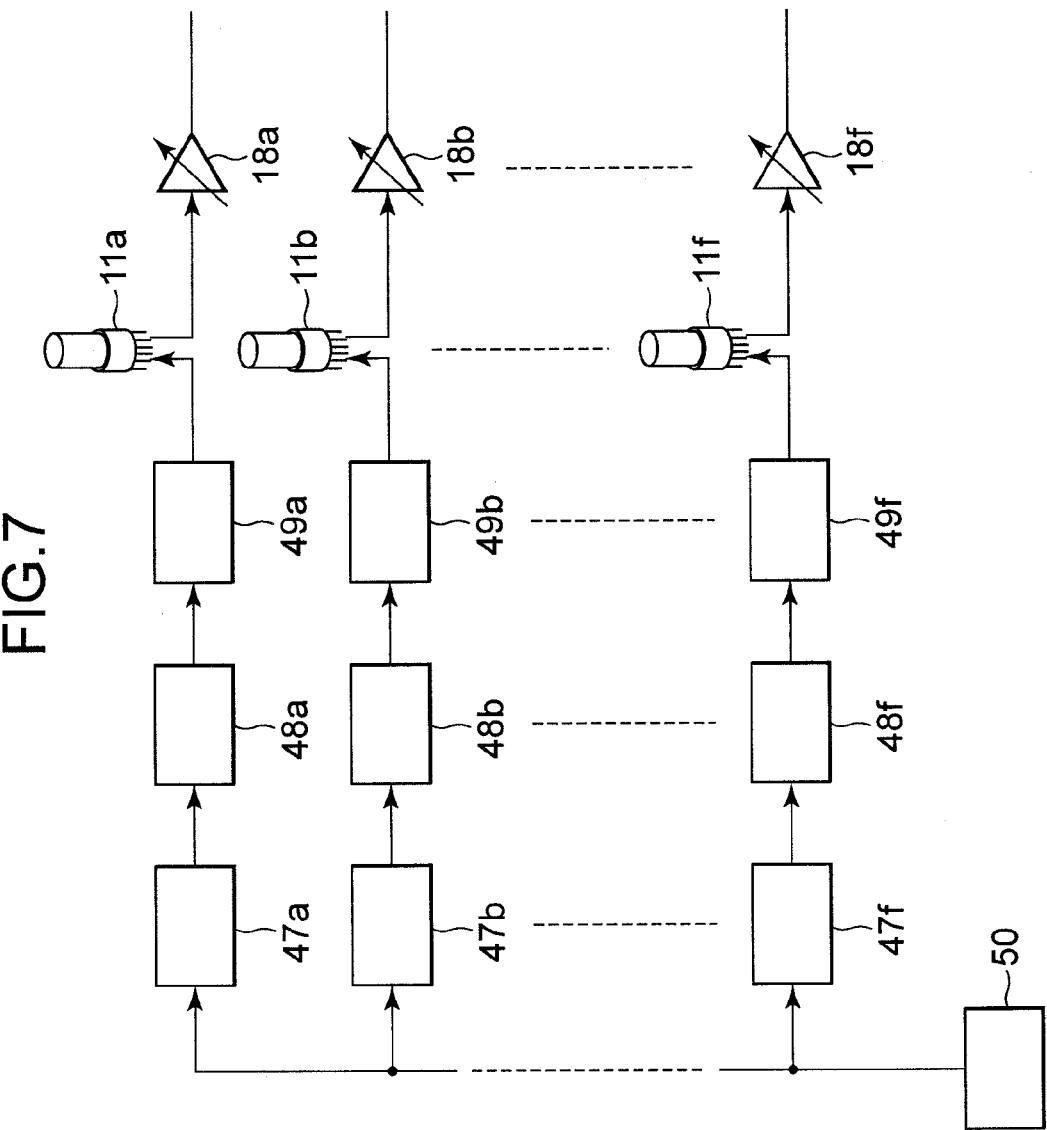
FIG. 7 is a diagram showing an example of means for controlling a sensitivity of a photomultiplier.

FIG. 7 shows an example of correcting the differences in sensitivity between the photomultipliers 11. Power units 49 (49a-49f) each control an applied high voltage according to input voltage. The high voltage can be supplied to each photomultiplier 11 by writing the voltage value into a latch 47 via an interface 50 and after converting this value into a voltage signal using a D-A converter 48, assigning the signal to the power unit 49. The sensitivity of the corresponding photomultiplier 11 can be controlled from a CPU by changing the voltage value to be written into the latch 47. In addition, combined use of amplification factor control by amplifiers 18 (18a-18o) facilitates the correction of the differences in sensitivity. For example, Model C4900, manufactured by Hamamatsu Photonics K.K., can be used as the power unit 49.

Figure 8:
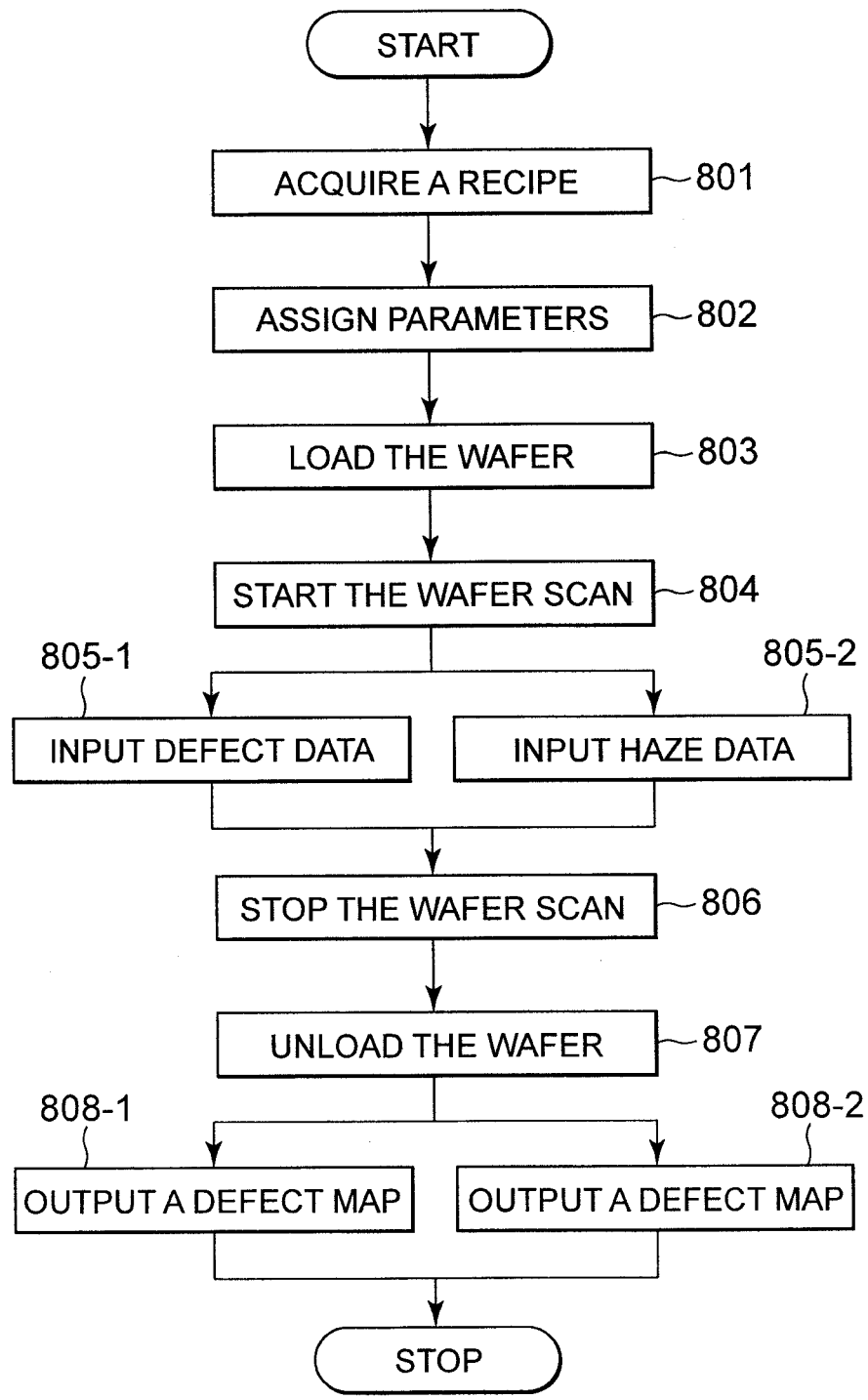
FIG. 8 is a diagram showing an example of an inspection flow in the inspection apparatus according to the present invention.

Next, an example of an inspection flow using the present inspection apparatus is described below using FIG. 8. First, an inspection recipe is acquired (step 801) and then a user assigns necessary parameters from a GUI screen to the apparatus (step 802). A wafer 1 is loaded onto the wafer stage 103 (step 803), and during illumination by the illumination optics, horizontally rotational scanning and rectilinear moving of the wafer 1 take place to start scans over its entire region (step 804). Defect data that has been obtained during the detection of forward scattered light is input from a defect memory (step 805-1), and haze data that has been obtained during the detection of sideward/backward scattered light is input from a haze memory (step 805-2). Upon completion of the inspection, the wafer scans (rotation and single-axis feed) are stopped (step 806) and the wafer 1 is unloaded (step 807). After this, a defect map and a haze map are displayed on the GUI screen as necessary (step 808).

Figure 9:
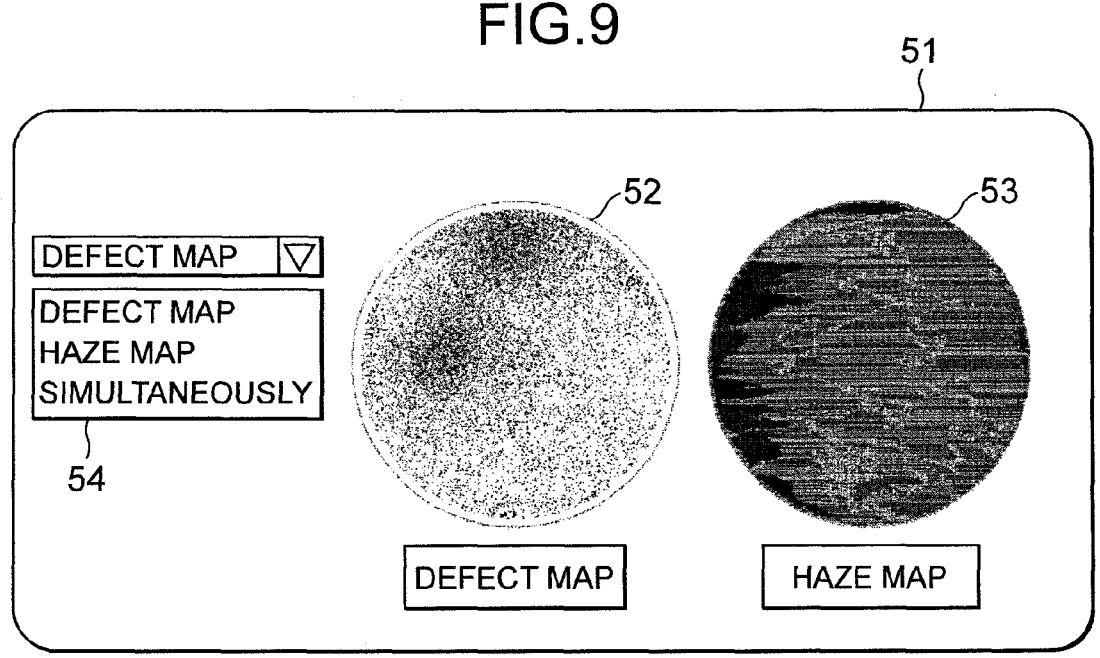
FIG. 9 is a diagram showing an example of a GUI screen display.

Step 802 includes a substep in which the user designates which of the multiple sets of detection optics (e.g., seven directions of low-angle detection optics A1-A7) is to be assigned to detecting forward or sideward/backward scattered light. In this substep, the optics sets A3, A4, A5 may be assigned to detecting forward scattered light, and the optics sets A1, A2, A6, A7 may be assigned to detecting sideward/backward scattered light. Also, step 804 includes a substep in which the scattered light is detected at a plurality of azimuth angle and elevation angle positions by the multiple sets of detection optics 102, and step 805 includes the above-described signal-processing step shown in FIG. 6. In addition, after the inspection, at least the defect map 52 or/and the haze map 53 are displayed on the GUI screen that the display unit 105 displays in step 808 as shown in FIG. 9, and a display map selection menu 50 for selecting the display of either or both of the two maps is also displayed when necessary.

Figure 10:
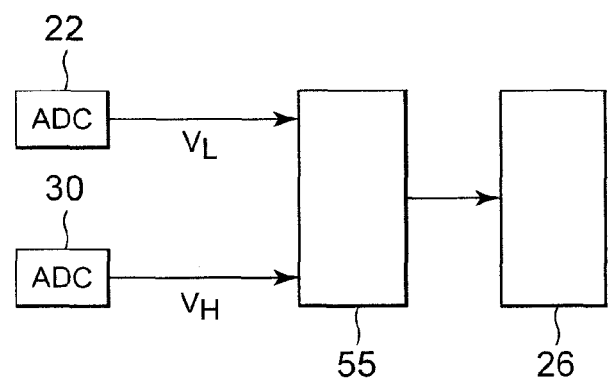
FIG. 10 is a diagram showing an example of a defect classification processing circuit.
Figure 11:
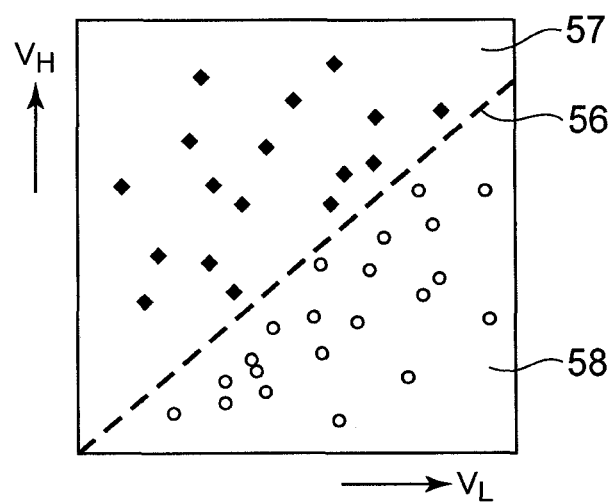
FIG. 11 is an illustrative diagram of defect classification details.

FIG. 10 is a diagram showing an example of defect discrimination by the present inspection apparatus. A detection signal $V_L$ is obtained by selecting one or more than one of the signals which have been detected by the multiple sets of low-angle detection optics, or by performing additions or other arithmetic operations upon all of these detected signals as appropriate. A detection signal $V_H$ is obtained by selecting one or more than one of the signals which have been detected by the multiple sets of high-angle detection optics or by performing additions or other arithmetic operations upon all of these detected signals as appropriate. The ratio between $V_L$ and $V_H$ is computed in a processing circuit 55 and the computed value is written into the defect memory 26. As shown in FIG. 11, if the computation result is plotted with $V_L$ on a horizontal axis and $V_H$ on a vertical axis, since concave defects such as crystal-originated pits (COPs) or scratches will be plotted in an upper area 57 from a threshold level curve 56, and convex defects such as contamination or other foreign substances, plotted in a lower area 58, appropriate discrimination of these concave and convex defects will be possible by setting the threshold level curve 56. Concave defects are usually defects that originally existed on silicon wafers or the like, and convex defects are usually defects that originated in the corresponding semiconductor-manufacturing apparatus. Even at the same defect density, therefore, if convex defects outnumber concave ones, this usually indicates that there is something problematic with the semiconductor-manufacturing apparatus.

While the invention by the present inventor has been described in detail above on the basis of an embodiment, the invention is not limited to the embodiment and it goes without saying that the invention can be changed or modified in other various forms without departing from the scope of the invention.

According to the present invention, an inspection apparatus can be provided that is able to detect microscopically smaller defects and to detect roughness very accurately.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes that come within the meaning and range of equivalency of the claims are therefore intended to be embraced therein.

What is claimed is:

1. An inspection method for detecting defects or haze of a sample, comprising the steps of:
    illuminating light to the sample from an oblique direction relative to a surface of the sample;
    detecting first scattered light at a forward position relative to an illuminating direction from the sample;
    detecting second scattered light at a sideward or backward position relative to the illuminating direction from the sample; and
    processing a first signal of the first scattered light and a second signal of the second scattered light with different weighting for the first signal and for the second signal.

2. The inspection method according to claim 1, wherein the processing step effects the different weighting in accordance with a noise intensity of the first signal and the second signal by relative comparison.

3. The inspection method according to claim 1, wherein the processing step effects the different weightings the first signal and the second signal in accordance with a difference in sensitivity between detectors for detecting the first scattered light and for detecting the second scattered light in advance.

4. The inspection method according to claim 1, wherein the processing step effects a greater weighting for the first signal than a weighting for the second signal.

5. The inspection method according to claim 4, wherein the processing step effects adding of the first signal which is weighted and the second signal which is weighted.

6. The inspection method according to claim 5, wherein the processing step detects defects in accordance with the added signals.

7. The inspection method according to claim 1, wherein the processing step effects a greater weighting for the second signal than a weighting for the first signal.

8. The inspection method according to claim 7, wherein the processing step effects adding of the first signal which is weighted and the second signal which is weighted.

9. The inspection method according to claim 8, wherein the processing step detects defects in accordance with the added signals.

10. The inspection method according to claim 9, wherein the processing step detects haze in accordance with the added signals.

11. The inspection method according to claim 1, wherein the processing step effects the weighting of the first signal and the second signal and detects defects or haze in accordance with the weighted signals.

12. An inspection apparatus for detecting defects or haze of a sample, comprising:
    an illuminator which illuminates light to the sample from an oblique direction relative to a surface of the sample;
    a first detector which detects first scattered light at a forward position relative to an illuminating direction from the sample;
    a second detector which detects second scattered light at a sideward or backward position relative to the illuminating direction from the sample;
    a processor which processes a first signal of the first scattered light and a second signal of the second scattered light with different weighting for the first signal and for the second signal.

13. The inspection apparatus according to claim 12, wherein the processor effects the different weighting in accordance with a noise intensity of the first signal and the second signal by relative comparison.

14. The inspection apparatus according to claim 12, wherein the processor effects the different weighting of the first signal and the second signal in accordance with a difference in sensitivity between the first and second detectors in advance.

15. The inspection apparatus according to claim 12, wherein the processor effects a greater weighting for the first signal than a weighting for the second signal.

16. The inspection apparatus according to claim 15, wherein the processor effects adding of the first signal which is weighted and the second signal which is weighted.

17. The inspection apparatus according to claim 16, wherein the processing step detects defects in accordance with the added signals.

18. The inspection apparatus according to claim 12, wherein the processor effects a greater weighting for the second signal than a weighting for the first signal.

19. The inspection apparatus according to claim 18, wherein the processor effects adding of the first signal which is weighted and the second signal which is weighted.

20. The inspection apparatus according to claim 19, wherein the processor detects defects in accordance with the added signals.

21. The inspection apparatus according to claim 19, wherein the processor detects haze in accordance with the added signals.

22. The inspection apparatus according to claim 12, wherein the processor effects the weighting of the first signal and the second signal and detects defects or haze in accordance with the weighted signals.

23. An inspection method for detecting defects or haze of a sample, comprising the steps of:
   illuminating light to the sample from an oblique direction relative to a surface of the sample;
   detecting first scattered light at a forward position relative to an illuminating direction from the sample;
   detecting second scattered light at a sideward or backward position relative to the illuminating direction from the sample; and
   processing a first signal of the first scattered light and a second signal of the second scattered light with different weighting for the first signal and for the second signal,
   wherein first detection optics detects the first scattered light scattering toward the forward position relative to the illuminating direction,
   wherein second detection optics detects the second scattered light scattering toward the sideward or backward position relative to the illuminating direction, and
   further comprising detecting haze by performing a first weighting process on the first and second signals and detecting defects by performing a second weighting process on the first and second signals.

24. The inspection method according to claim 23, further comprising detecting haze by weighting the first signal of the detected first scattered light scattering toward the forward direction more than weighting the second signal of the detected second scattered light scattering toward the sideward or backward direction.

25. The inspection method according to claim 23, further comprising detecting defects by weighting the second signal of the detected scattered light scattering in at least one of the sideward or backward positions more than weighting the first signal of the detected scattered light scattering in the forward position.

26. The inspection method according to claim 23, further comprising detecting haze by weighting the first signal of the detected first scattered light scattering toward the forward direction more than weighting the second signal of the detected second scattered light scattering toward the sideward or backward direction, and
   detecting defects by weighting the second signal of the detected scattered light scattering in at least one of the sideward or backward positions more than weighting the first signal of the detected scattered light scattering in the forward position.

* * * * *